United States Patent
Mukaibatake

(10) Patent No.: US 8,653,447 B2
(45) Date of Patent: Feb. 18, 2014

(54) CHROMATOGRAPH MASS SPECTROMETER

(75) Inventor: Kazuo Mukaibatake, Kyoto (JP)

(73) Assignee: Shimadzu Corporation, Kyoto-Shi (JP)

( * ) Notice: Subject to any disclaimer, the term of this patent is extended or adjusted under 35 U.S.C. 154(b) by 0 days.

(21) Appl. No.: 13/997,550

(22) PCT Filed: Dec. 28, 2010

(86) PCT No.: PCT/JP2010/073749
§ 371 (c)(1),
(2), (4) Date: Jun. 24, 2013

(87) PCT Pub. No.: WO2012/090308
PCT Pub. Date: Jul. 5, 2012

(65) Prior Publication Data
US 2013/0284919 A1    Oct. 31, 2013

(51) Int. Cl.
*B01D 59/44* (2006.01)
*H01J 49/00* (2006.01)

(52) U.S. Cl.
USPC ........... 250/281; 250/282; 250/283; 250/287; 250/288; 250/289; 250/290; 250/291; 250/292

(58) Field of Classification Search
USPC ................................ 250/281–283, 287–292
See application file for complete search history.

(56) References Cited

U.S. PATENT DOCUMENTS

2011/0073756 A1* 3/2011 Mukaibatake et al. ....... 250/290
2011/0101221 A1* 5/2011 Mukaibatake et al. ....... 250/292

FOREIGN PATENT DOCUMENTS

JP    2000304735 A    11/2000
JP    2007323838 A    12/2007

OTHER PUBLICATIONS

International Search Report mailed Feb. 1, 2011 for International Application No. PCT/JP2010/073749 (2 pages).

* cited by examiner

*Primary Examiner* — Jack Berman
*Assistant Examiner* — Meenakshi Sahu
(74) *Attorney, Agent, or Firm* — Bingham McCutchen LLP

(57) ABSTRACT

When an SIM measurement for ions originating from a target component separated by a chromatograph is performed, the measurement is performed while the mass-resolving power is switched among a plurality of levels of resolving power, with the mass-to-charge ratio fixed at a target value (S2), and an extracted ion chromatogram is created based on each of data obtained corresponding to respective mass-resolving powers (S3). After the extracted ion chromatograms are obtained, an S/N ratio is calculated for a peak of the target component on each of the chromatograms (S4), and a mass-resolving power which yields the highest S/N ratio is selected (S5). The selected mass-resolving power is set as the mass-resolving power in the subsequent measurements of the same target component in the same kind of sample (S6), and the quantitative determination of the target component is performed using the extracted ion chromatogram obtained with the selected mass-resolving power (S7).

11 Claims, 3 Drawing Sheets

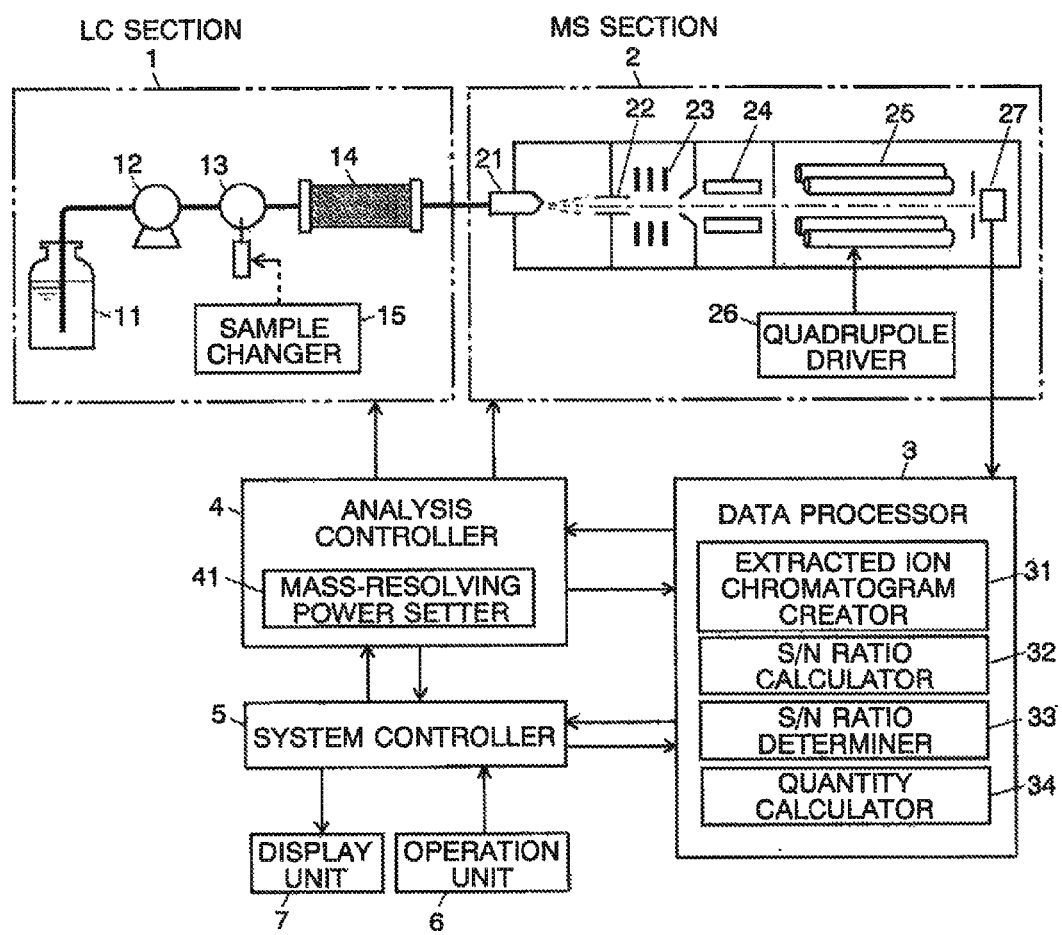

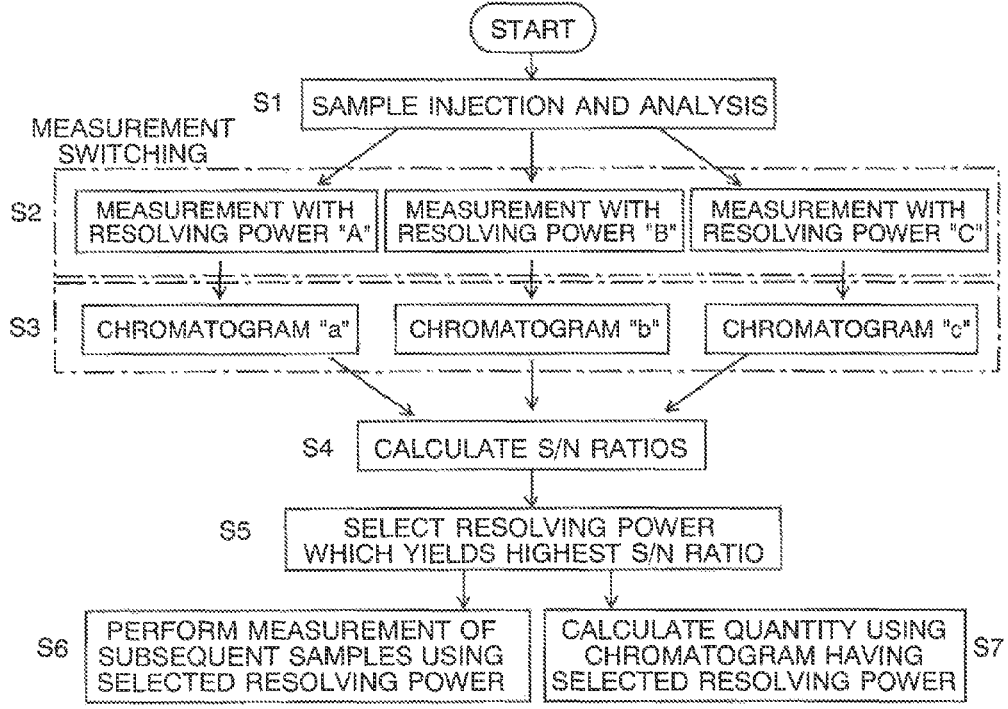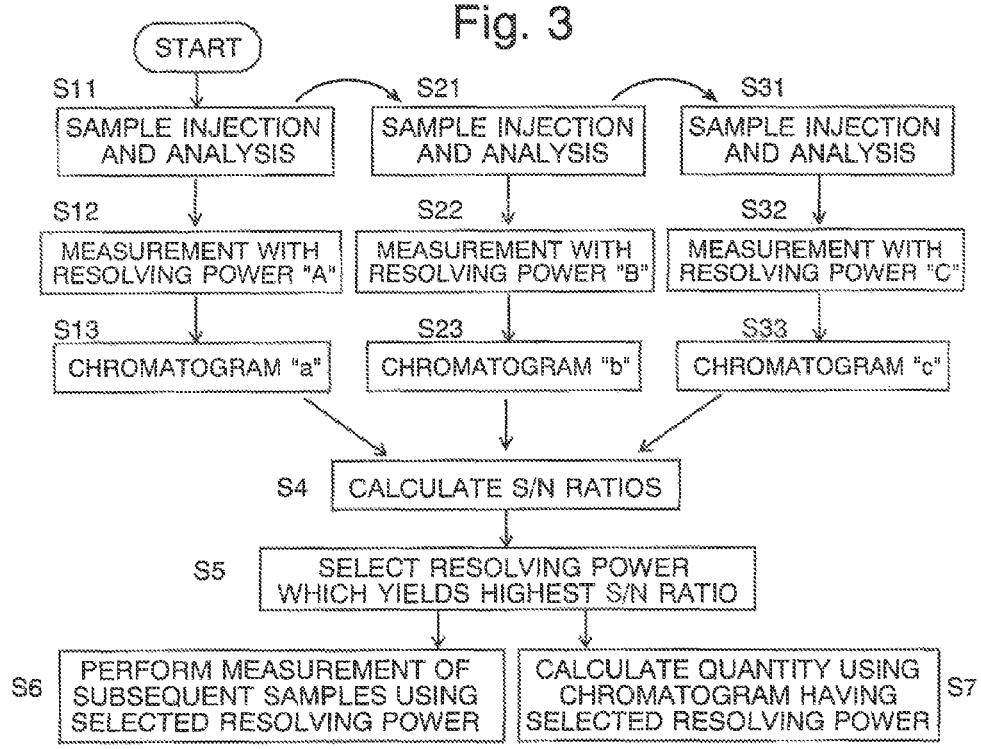

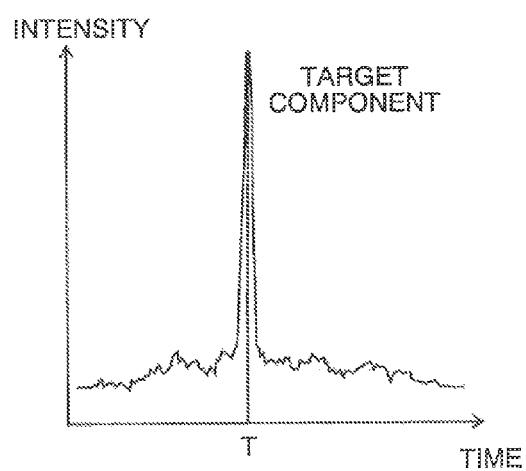 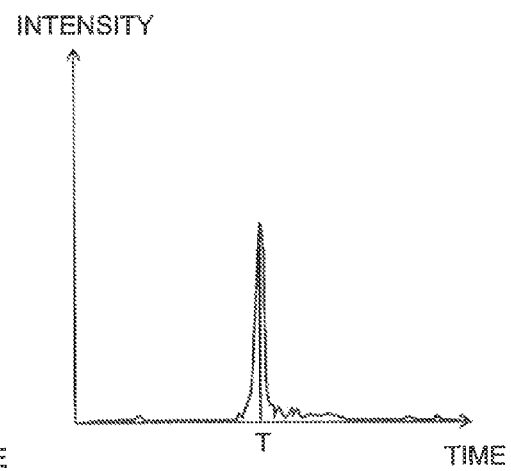

CHROMATOGRAPH MASS SPECTROMETER

TECHNICAL FIELD

The present invention relates to a chromatograph mass spectrometer in which a chromatograph for separating the components of a sample in the temporal direction is combined with a quadrupole mass spectrometer using a quadrupole mass filter as a mass analyzer for separating ions according to their mass-to-charge ratios (m/z). The "quadrupole mass spectrometer" in the present invention includes triple quadrupole mass spectrometers having two quadrupole mass filters with a collision cell in between so as to perform an MS/MS analysis, not to mention mass spectrometers having a single quadrupole mass filter.

BACKGROUND ART

The quadrupole mass spectrometer, which uses a quadrupole mass filter as the mass analyzer, is one of the most widely used types of mass spectrometers because it is small in size and comparatively inexpensive. In quadrupole mass spectrometers, a direct-current voltage and a radio-frequency voltage are applied to each of the four rod electrodes constituting a quadrupole mass filter to create a quadrupole electric field within the space surrounded by the rod electrodes. This electric field oscillates ions while they are travelling through it, causing the ions which do not conform to specific conditions to be dispersed and removed halfway.

In general, a sample to be analyzed contains various foreign substances other than the target components. To perform qualitative and/or qualitative analysis of target components without being influenced by such foreign substances, chromatograph mass spectrometers, in which a mass spectrometer as previously described is combined with a chromatograph, such as a liquid chromatograph or gas chromatograph, are used. When a chromatograph mass spectrometer is used for a quantitative analysis of known target components, since the mass-to-charge ratio of each target component to be observed is known, the mass spectrometer is operated in a selected ion monitoring (SIM) measurement mode for repeatedly observing the intensity of the ions, focusing on one or a plurality of specific mass-to-charge ratios of interest. Using the data obtained by such a measurement, a data processing system creates an extracted ion chromatogram (which may also be called a mass chromatogram) which shows the relationship between the elapsed time and the ion intensity at the specific mass-to-charge ratio or ratios, then calculates the area of a peak appearing on that chromatogram at or near the retention time of a target component, and converts the area into the content of the target component (for example, see Patent Document 1). To enhance the quality of quantitative determination of target components by a chromatograph mass spectrometer, it is essential to improve the quality of the extracted ion chromatogram, or specifically, the S/N ratio of the chromatogram.

In a quadrupole mass spectrometer, the mass-resolving power can be regulated by changing the ratio between the radio-frequency voltage and the direct-current voltage applied to the rod electrodes of the quadrupole mass filter. Conventional chromatograph mass spectrometers also have such a function and allow users to set the mass-resolving power for the SIM measurement. Normally, improving the mass-resolving power enhances the ion selectivity and makes the ion in question less affected by interference from other ions having close mass-to-charge ratios. However, it also decreases the amount of ions to be reflected in the peak, which lowers the intensity of the ion and deteriorates the sensitivity.

Thus, a trade-off between the mass-resolving power and the sensitivity exists in the setting of the mass-resolving power. There is no general rule for determining whether the sensitivity should be to some extent sacrificed to improve the mass-resolving power and thereby enhance the quality of the extracted ion chromatogram (which is required for a better determination of the quantities of target components, as already explained), or conversely, the mass-resolving power should be to some extent sacrificed to improve the sensitivity. This is because it depends on the kind and state of the sample to be analyzed, the analysis conditions (e.g. the kind of mobile phase used in the chromatograph), and other factors. Until the sample is actually measured and data are collected, it is impossible to know what level of mass-resolving power is appropriate for obtaining a high-quality extracted ion chromatogram. Accordingly, to optimize the quality of quantitative determination, users need to perform the measurement a plurality of times and find an appropriate mass-resolving power.

This problem also occurs in the case of performing an MS/MS analysis in a multiple reaction monitoring (MRM) measurement mode or selected reaction monitoring (SRM) measurement mode using a triple quadrupole mass spectrometer as the detector for a chromatograph. In this case, users can set both the mass-resolving power of the first quadrupole mass filter and that of the second quadrupole mass filter. Accordingly, to optimize the quality of quantitative determination, they need to do an even more cumbersome task of performing the measurement a plurality of times while changing the combination of the mass-resolving powers of the first and second mass filters.

BACKGROUND ART DOCUMENT

Patent Document

Patent Document 1: JP-A 2000-304735

SUMMARY OF THE INVENTION

Problem to be Solved by the Invention

The present invention has been developed to solve the previously described problem, and its primary objective is to provide a chromatograph mass spectrometer capable of obtaining an extracted ion chromatogram under an appropriate mass-resolving power, without requiring users to perform a cumbersome and complex task. The secondary objective of the present invention is to provide a chromatograph mass spectrometer capable of setting an appropriate mass-resolving power and performing a quantitative analysis with a high degree of accuracy and a high level of reproducibility, without requiring users to perform cumbersome and complex tasks.

Means for Solving the Problems

The first aspect of the present invention aimed at solving the aforementioned problem is a chromatograph mass spectrometer having a chromatograph in which components of a sample are separated in a temporal direction and a mass spectrometer with a quadrupole mass filter in which ions originating from the components of the sample separated by the chromatograph are separated according to the mass-to-charge ratios thereof, the chromatograph mass spectrometer including:

a) a quadrupole driver for applying a direct-current voltage and a radio-frequency voltage to each electrode constituting the quadrupole mass filter, so as to selectively allow an ion having a specific mass-to-charge ratio to pass through;

b) a controller for controlling the quadrupole driver so as to change the applied voltages in such a manner that the mass-resolving power is sequentially switched among a plurality of previously determined levels of mass-resolving power when a target ion originating from a target component is allowed to pass through the quadrupole mass filter and be detected; and c) a chromatogram creator for creating an extracted ion chromatogram based on each of a plurality of data obtained under conditions with different levels of mass-resolving power set for the target ion.

In the chromatograph mass spectrometer according to the first aspect of the present invention, a mass spectrometry is performed for one or a plurality of target components while sequentially switching the mass-resolving power for one introduction of the sample into the chromatograph, and an extracted ion chromatogram is obtained for each level of mass-resolving power. Even if an appropriate level of mass-resolving power for obtaining a chromatographic peak of each component is unknown beforehand, or if the appropriate mass-resolving power is different for each of a plurality of components contained in the sample, it is possible, for example, to assuredly obtain an extracted ion chromatogram with reduced influence from foreign substances, or an extracted ion chromatogram with a higher detection sensitivity, for each target component. Accordingly, there is no need to perform the measurement a plurality of times while changing the setting of the mass-resolving power, and the workload on the user is reduced. Furthermore, the situation where the amount of sample is insufficient for performing the measurement a plurality of times can be dealt with.

In a preferable mode of the first aspect of the present invention, the chromatograph mass spectrometer further includes:

d) a chromatogram evaluator for extracting a peak corresponding to the target component on each of the extracted ion chromatograms created by the chromatogram creator, for calculating an S/N ratio of each of the peaks, and for comparing the S/N ratios to select, as an optimal condition, a mass-resolving power which yields the highest S/N ratio.

In this system, for each of the extracted ion chromatograms created by the chromatogram creator, the chromatogram evaluator extracts a peak corresponding to the target ion, calculates the S/N ratio of each peak, and compares the calculated S/N ratios to find the mass-resolving power which gives the highest S/N ratio. In the calculation of the S/N ratios of the peaks, for example, the intensity value at the top of the detected peak may be used as the signal value (S), while the noise value (N) may be calculated by using the values of all the measurement points exclusive of the peak section (between the beginning and ending points of the peak). Needless to say, the method of determining S and N in the calculation of the S/N ratio is not limited to this one.

The mass-resolving power with which the extracted ion chromatogram having the highest S/N ratio has been obtained can be regarded as an optimal level of mass-resolving power, at least for an analysis in which the same target component (compound) is analyzed under the same conditions. Accordingly, in one mode of the first aspect of the present invention, the chromatograph mass spectrometer further includes an automatic analysis-condition setter for setting, as an analysis condition, the mass-resolving power selected as the optimal condition by the chromatogram evaluator, so as to perform a mass spectrometry for an ion originating from the aforementioned sample component or a mass spectrometry for a sample containing the target component.

With this system, for example, when a number of the same kind of samples prepared beforehand are sequentially subjected to a measurement under the same conditions, the mass-resolving power which yields the highest S/N ratio can be determined in the first measurement, after which the measurements of the subsequent samples can be performed under that condition.

In another mode of the first aspect of the present invention, the chromatograph mass spectrometer further includes a quantity calculator for determining the quantity of the target component by using the extracted ion chromatogram corresponding to the mass-resolving power selected as the optimal condition by the chromatogram evaluator. This system can assuredly determine the most accurate quantitative value.

The second aspect of the present invention aimed at solving the aforementioned problem is a chromatograph mass spectrometer having a chromatograph in which components of a sample are separated in a temporal direction and a mass spectrometer with a quadrupole mass filter in which ions originating from the components of the sample separated by the chromatograph are separated according to the mass-to-charge ratios thereof, the chromatograph mass spectrometer including:

a) a quadrupole driver for applying a direct-current voltage and a radio-frequency voltage to each electrode constituting the quadrupole mass filter, so as to selectively allow an ion having a specific mass-to-charge ratio to pass through;

b) a controller for controlling the quadrupole driver so as to change the applied voltages in such a manner that a plurality of levels of mass-resolving power previously determined for one sample is sequentially selected in a repetition of analyzing operations for the same sample so that a mass spectrometry is performed with each of the plurality of levels of mass-resolving power;

c) a chromatogram creator for creating an extracted ion chromatogram based on each of a plurality of data obtained under conditions with different levels of mass-resolving power set for the same sample, each of the extracted ion chromatograms including at least a peak corresponding to the same target component in the sample; and d) a chromatogram evaluator for extracting the peak corresponding to the target component on each of the extracted ion chromatograms created by the chromatogram creator, for calculating an S/N ratio of each of the peaks, and for comparing the S/N ratios to select, as an optimal condition, a mass-resolving power which yields the highest S/N ratio.

In the chromatograph mass spectrometer according to the second aspect of the present invention, the same sample is introduced into the chromatograph a plurality of times. For each introduction of the sample, the mass-resolving power is switched to a different level, and an extracted ion chromatogram is obtained for each level of mass-resolving power. In this case, the analysis for the same sample is repeated as many times as the number of levels of mass-resolving power to be sequentially selected. Similar to the first aspect of the present invention, in the chromatograph mass spectrometer according to the second aspect of the present invention, the same number of extracted ion chromatograms as the number of levels of mass-resolving power are obtained, with each extracted ion chromatogram obtained with a different mass-resolving power for the target component. For each of the extracted ion chromatograms, the chromatogram evaluator extracts a peak corresponding to the target component, calculates the S/N ratio of each peak, and compares the calculated S/N ratios to find the mass-resolving power which gives the highest S/N ratio.

It is possible to provide the second aspect of the present invention with the same configuration as the previously described two modes of the first aspect of the present invention and thereby achieve the same operations and effects.

In one possible embodiment of the chromatograph mass spectrometer according to the first or second aspect of the present invention, the mass spectrometer has a single quadrupole mass filter, and the controller conducts a mass spectrometry of the target component in a selected ion monitoring (SIM) measurement mode.

In another possible embodiment of the chromatograph mass spectrometer according to the first or second aspect of the present invention, the mass spectrometer has two of the quadrupole mass filters respectively provided before and after a collision cell, and the controller conducts an MS/MS analysis of the target component in a multiple reaction monitoring measurement mode or selected reaction monitoring measurement mode while changing the combination of the mass-resolving power of the first quadrupole mass filter and the mass-resolving power of the second quadrupole mass filter.

Effect of the Invention

With the chromatograph mass spectrometer according to the first aspect of the present invention, it is possible to create an appropriate extracted ion chromatogram for one or a plurality of target components by a single introduction of a sample into the chromatograph, without requiring users to perform cumbersome settings or tasks. Furthermore, by additionally providing the chromatograph mass spectrometer according to the first aspect of the present invention with the chromatogram evaluator, or by using the chromatograph mass spectrometer according to the second aspect of the present invention, it is possible to determine the quantity of a target component with high accuracy, without requiring users to perform cumbersome settings or tasks. Furthermore, for example, in the case where the quantity determination of a target component is performed for each of a number of the same kind of samples all of which contain that target component, the quantities can be accurately determined with a high level of throughput.

BRIEF DESCRIPTION OF THE DRAWINGS

FIG. 1 is a configuration diagram showing the main components a liquid chromatograph mass spectrometer (LC/MS) as one embodiment of the present invention.

FIG. 2 is a flowchart of analyzing operations and process steps in the LC/MS of the present embodiment.

FIG. 3 is a flowchart of analyzing operations and process steps in the LC/MS as another embodiment of the present invention.

FIGS. 4A and 4B are examples of extracted ion chromatograms obtained with different mass-resolving powers, where FIG. 4A is the case of a low mass-resolving power and FIG. 4B is the case of a high mass-resolving power.

BEST MODE FOR CARRYING OUT THE INVENTION

A liquid chromatograph mass spectrometer (LC/MS) as one embodiment of the present invention is hereinafter described with reference the attached drawings.

FIG. 1 is a configuration diagram showing the main components of the LC/MS according to the present embodiment. The LC/MS of the present embodiment includes a liquid chromatograph (LC) section 1 for separating various components of a sample in the temporal direction, and a mass spectrometer (MS) section 2 for performing a mass spectrometry of each of the separated sample components.

The LC section 1 includes a mobile-phase container 11 in which a mobile phase is stored, a liquid-sending pump 12 for drawing the mobile phase and for sending it at a constant flow rate, an injector 13 for injecting a sample into the mobile phase at a predetermined timing, a column 14 for separating various components of the sample in the temporal direction, and a sample changer 15 for sequentially selecting a plurality of prepared samples in predetermined order and for giving the selected sample to the injector 13.

The MS section 2 includes an electrostatic spray 12 for ionizing an eluate containing sample components eluted from the column 14 by electrostatic atomization in an atmospheric ambience, a heated capillary 22 for guiding ions originating from the sample components into a vacuum ambience, ion guides 23 and 24 for transporting the ions to the subsequent stage while focusing them, a quadrupole mass filter 25 consisting of four rod electrodes, a quadrupole driver 26 for applying a predetermined voltage to each of the rod electrodes of the quadrupole mass filter 25 so as to allow ions having a specific mass-to-charge ratio to pass through, as well as a detector 27 for detecting ions that have passed through the quadrupole mass filter 25.

Though not shown, the quadrupole driver 26 includes a direct-current voltage generator, a radio-frequency voltage generator, and an adder for adding the radio-frequency voltage and the direct-current voltage. It applies a voltage $U+V\cos\Omega t$, which is produced by adding a direct-current voltage $U$ and a radio-frequency voltage $V\cos\Omega t$, to one pair of the rod electrodes facing each other across the ion beam axis among the four rod electrodes, and another voltage $-U-V\cos\Omega t$, which is produced by adding a direct-current voltage $-U$ having the same absolute value of the voltage with opposite polarity and a radio-frequency voltage $-V\cos\Omega t$ having the same amplitude with opposite polarity (with reversed phase), to the other pair of the rod electrodes. In some cases, a common direct-current bias voltage is also applied to all the rod electrodes.

The detection signal produced by the detector 27 of the MS section 2 is sent to a data processor 3, which converts the signals into digital values and performs a data processing to create a mass spectrum or chromatogram, or to perform a quantitative analysis. The data processor 3 includes, as functional blocks characteristic of the present invention, an extracted ion chromatogram creator 31, an S/N ratio calculator 32, an S/N ratio determiner 33 and a quantity calculator 34. An analysis controller 4, which controls the operations of the LC section 1, the MS section 2 and the data processor 3, includes a mass-resolving power setter 41 as a functional block characteristic of the present invention. A system controller 5, with an operation unit 6 and a display unit 7 connected thereto, mainly functions as a user interface through those units. The functions of the data processor 3, the analysis controller 4 and the system controller 5 can be realized by using a personal computer including a central processing unit, a memory and other components as hardware, and by executing a preinstalled controlling and processing software program on that personal computer.

FIG. 2 is a flowchart of analyzing operations and process steps in the LC/MS of the present embodiment. For ease of explanation, the following description deals with the case of determining the quantity of a single target component contained in a sample.

After setting the measurement mode in the MS section 2 to the SIM measurement mode, a user (operator) specifies, as the analyzing conditions, the mass-to-charge ratio M corresponding to the target component, a predicted retention time T of the target component, a measurement time range (i.e. starting time ts and ending time te, where ts<T<te), and other parameters through the operation unit 6. The user also specifies a plurality of levels of mass-resolving power for mass spectrometry. In the present example, three different mass-resolving powers A, B and C are specified. When the analysis is initiated, the first sample selected by the sample changer 15 under the control of the analysis controller 4 is injected into the mobile phase by the injector 13. While the sample is passing through the column 14, the sample components are temporally separated and eluted (Step S1).

In the MS section 2, a mass spectrometry with the mass-to-charge ratio M as the target is repeated at predetermined intervals of time during the period from starting time ts to ending time te. That is to say, the quadrupole driver 26 sets the direct-current voltages and the radio-frequency voltages applied to the rod electrodes so that the ions of mass-to-charge ratio M are selectively allowed to pass through at predetermined intervals of time and the mass-resolving power is sequentially switched to A, B and C within each cycle of the measurement performed at the predetermined intervals of time (Step S2). From the starting time ts on, the extracted ion chromatogram creator 31 receives data extracted from the signals produced by the detector 27, sorts the data into three groups: the data obtained under the quadrupole drive condition of mass-resolving power A, the data obtained under the quadrupole drive condition of mass-resolving power B, and the data obtained under the quadrupole drive condition of mass-resolving power C, and creates an extracted ion chromatogram at the mass-to-charge ratio M based on each group of data (Step S3).

When the predicted retention time T approaches with the elapse of time from the point of sample injection, the target component begins to be eluted from the exit of the column 14. The ions with mass-to-charge ratio M originating from the target component pass through the quadrupole mass filter 25 and reach the detector 27 while the aforementioned voltages are applied to the rod electrodes of the quadrupole mass filter 25. Accordingly, a peak begins to appear on each of the extracted ion chromatograms, with the peak top at around the predicted retention time T, after which the ion intensity decreases and the peak comes to an end. When the ending time to is reached, the extracted ion chromatogram creator 31 discontinues the creation of the extracted ion chromatograms. As a result, three extracted ion chromatograms a, b and c which respectively correspond to the mass-resolving powers A, B and C are obtained.

FIGS. 4A and 4B are examples of extracted ion chromatograms obtained with different mass-resolving powers, where FIG. 4A is the case of a low mass-resolving power and FIG. 4B is the case of a high mass-resolving power. Under the condition that there are a lot of foreign substances having mass-to-charge ratios close to the mass-to-charge ratio M of the ions of interest, when the mass-resolving power is lowered, a portion of the ions of the foreign substances are reflected in the ion intensity, causing the noise to increase to considerable levels, although the signal intensity of the peak also becomes high, as shown in FIG. 4A. By contrast, when the mass-resolving power is increased, the influences of the foreign substances are eliminated. However, this operation also excludes a portion of the ions of interest, causing the signal intensity of the peak to be considerably lower than the level observed under the low mass-resolving power.

The S/N ratio calculator 32 calculates the S/N ratio of the peak of the target ion for each of the extracted ion chromatograms a, b and c (Step S4). For example, the S/N ratio is calculated by determining the intensity value at the top of the peak of the target ion on the extracted ion chromatogram as the signal value (S) while calculating the noise value (N) using the values of all the measurement points exclusive of the peak section (between the beginning to ending points of the peak). Needless to say, the method of determining S and N in the calculation of the S/N ratio is not limited to this one. The S/N ratio determiner 33 compares the S/N ratios calculated for each of the extracted ion chromatograms and selects a mass-resolving power which has yielded the highest S/N ratio (Step S5). Information relating to the selected mass-resolving power (i.e. information about which of the three levels A, B and C has been selected) is sent to the analysis controller 4. The mass-resolving power setter 41 receives this information and sets the thereby indicated mass-resolving power as the mass-resolving power to be used as one of the analysis conditions for the second and subsequent samples of the same kind (the samples having the same target component). In the subsequent mass spectrometry, the mass spectrometry for the target component in the SIM measurement mode will be performed using the set mass-resolving power (Step S6).

In general, blood (plasma, serum or the like), urine, food samples and similar stuff contain a lot of foreign substances (matrix components) other than target components. In such a case, the S/N ratio is likely to increase when the mass-resolving power is increased so as to enhance the selectivity of an ion originating from the target component. Conversely, in the case of a chemically synthesized compound or similar sample containing only a small amount of foreign substances, the S/N ratio is likely to become high when the mass-resolving power is lowered so as to increase the ion intensity while sacrificing the ion selectivity.

The quantity calculator 34 calculates the quantity of the target component, using the extracted ion chromatogram obtained under the selected mass-resolving power (Step S7). That is to say, it calculates the area value of the peak corresponding to the target component on that extracted ion chromatogram and determines the content of the target component from the area value with reference to a previously created calibration curve showing the relationship between the area value and the content (concentration). Since the quantitative determination is performed using the extracted ion chromatogram having the highest S/N ratio, the quantity values can be determined with a high level of accuracy.

Each target component is differently influenced by foreign substances. Therefore, when the quantities of a plurality of target components are to be determined, it is preferable to set a plurality of levels of mass-resolving power for each target component, calculate the S/N ratios of the extracted ion chromatograms obtained under the plurality of levels of mass-resolving power, and find the mass-resolving power which gives the highest S/N ratio for that component. In this case, each of the components to be analyzed in one sample may possibly have a different mass-resolving power regarded as optimal.

Analyzing operations and process steps in an LC/MS as another embodiment of the present invention are hereinafter described with reference to the flowchart of FIG. 3.

In the previous embodiment, the measurements under the three mass-resolving powers A, B and C are repeated, and one extracted ion chromatogram is obtained for each mass-resolving power in a single set of injection and analysis of the sample. By contrast, in the present embodiment, the injector 13 and the sample changer 15 under the control of the analysis controller 4 repeat the injection and analysis of the same sample the same number of times as the levels of mass-resolving power (three times in the previous example). That is to say, in the first round of injections and analyses of the sample (Step S11), the MS section 2 repeats a mass spectrometry with the mass-to-charge ratio M as the target at predetermined intervals of time during the period from starting time ts to ending time te, with the mass-resolving power fixed at A (Step S12). During this period, the extracted ion chromatogram creator 31 receives data extracted from the signals produced by the detector 27 and creates an extracted ion chromatogram "a" at the mass-to-charge ratio M based on those data (Step S13).

In the second round of injections and analyses of the sample (Step S21), the MS section 2 repeats the mass spectrometry with the mass-to-charge ratio M as the target at predetermined intervals of time during the period from starting time ts to ending time te, with the mass-resolving power fixed at B (Step S22). During this period, the extracted ion chromatogram creator 31 receives data extracted from the signals produced by the detector 27 and creates an extracted ion chromatogram "b" at the mass-to-charge ratio M based on those data (Step S23). In the third round of injections and analyses of the sample (Step S31), the MS section 2 repeats the mass spectrometry with the mass-to-charge ratio M as the target at predetermined intervals of time during the period from starting time ts to ending time te, with the mass-resolving power fixed at C (Step S32). During this period, the extracted ion chromatogram creator 31 receives data extracted from the signals produced by the detector 27 and creates an extracted ion chromatogram "c" at the mass-to-charge ratio M based on those data (Step S33).

After the three extracted ion chromatograms "a", "b" and "c" have been created by the three rounds of analyses, the S/N ratio calculator 32 calculates the S/N ratio of the peak corresponding to the target component on each of the extracted ion chromatograms (Step S4), and compares the S/N ratios to select a mass-resolving power which yields the highest S/N ratio (Step S5), as in the previous embodiment. The processes of Steps S6 and S7 are also similar to those of the previous embodiment.

Although the MS section 2 in the previous embodiment has a single quadrupole mass filter 25, it is natural that the present invention can also be applied in the case where the MS section 2 is a triple quadrupole mass spectrometer having two quadrupole mass filters with a collision cell in between. When the MS section 2 is a triple quadrupole mass spectrometer, the mass-resolving power of the first quadrupole mass filter and that of the second quadrupole mass filter can be independently set and there are various possible combinations of the mass-resolving powers of the first and second mass filters. Accordingly, an even larger number of extracted ion chromatograms will be obtained for the same target component (or the same sample).

It should be noted that the previous embodiments are mere examples of the present invention, and any change, addition or modification appropriately made within the spirit of the present invention will evidently fall within the scope of claims of the present patent application.

EXPLANATION OF NUMERALS

1... Liquid Chromatograph (LC) Section
11... Mobile Phase Container
12... Liquid-Sending Pump
13... Injector
14... Column
15... Sample Changer
2... Mass Spectrometer (MS) Section
21... Electrostatic Spray
22... Heated Capillary
23, 24... Ion Guide
25... Quadrupole Mass Filter
26... Quadrupole Driver
27... Detector
3... Data Processor
31... Extracted Ion Chromatogram Creator
32... S/N Ratio Calculator
33... S/N Ratio Determiner
34... Quantity Determiner
4... Analysis Controller
41... Mass-Resolving Power Setter
5... System Controller
6... Operation Unit
7... Display Unit

The invention claimed is:

1. A chromatograph mass spectrometer having a chromatograph in which components of a sample are separated in a temporal direction and a mass spectrometer with a quadrupole mass filter in which ions originating from the components of the sample separated by the chromatograph are separated according to mass-to-charge ratios thereof, the chromatograph mass spectrometer comprising:
   a) a quadrupole driver for applying a direct-current voltage and a radio-frequency voltage to each electrode constituting the quadrupole mass filter, so as to selectively allow an ion having a specific mass-to-charge ratio to pass through;
   b) a controller for controlling the quadrupole driver so as to change the applied voltages in such a manner that a mass-resolving power is sequentially switched among a plurality of previously determined levels of mass-resolving power when a target ion originating from a target component is allowed to pass through the quadrupole mass filter and be detected; and
   c) a chromatogram creator for creating an extracted ion chromatogram based on each of a plurality of data obtained under conditions with different levels of mass-resolving power set for the target ion.

2. The chromatograph mass spectrometer according to claim 1, further comprising:
   d) a chromatogram evaluator for extracting a peak corresponding to the target component on each of the extracted ion chromatograms created by the chromatogram creator, for calculating an S/N ratio of each of the peaks, and for comparing the S/N ratios to select, as an optimal condition, a mass-resolving power which yields the highest S/N ratio.

3. A chromatograph mass spectrometer having a chromatograph in which components of a sample are separated in a temporal direction and a mass spectrometer with a quadrupole mass filter in which ions originating from the components of the sample separated by the chromatograph are separated according to mass-to-charge ratios thereof, the chromatograph mass spectrometer comprising:
   a) a quadrupole driver for applying a direct-current voltage and a radio-frequency voltage to each electrode constituting the quadrupole mass filter, so as to selectively allow an ion having a specific mass-to-charge ratio to pass through;

b) a controller for controlling the quadrupole driver so as to change the applied voltages in such a manner that a plurality of levels of mass-resolving power previously determined for one sample is sequentially selected in a repetition of analyzing operations for a same sample so that a mass spectrometry is performed with each of the plurality of levels of mass-resolving power;

c) a chromatogram creator for creating an extracted ion chromatogram based on each of a plurality of data obtained under conditions with different levels of mass-resolving power set for the same sample, each of the extracted ion chromatograms including at least a peak corresponding to a same target component in the sample; and d) a chromatogram evaluator for extracting the peak corresponding to the target component on each of the extracted ion chromatograms created by the chromatogram creator, for calculating an S/N ratio of each of the peaks, and for comparing the S/N ratios to select, as an optimal condition, a mass-resolving power which yields the highest S/N ratio.

4. The chromatograph mass spectrometer according to claim 2, further comprising:

an automatic analysis-condition setter for setting, as an analysis condition, the mass-resolving power selected as the optimal condition by the chromatogram evaluator, so as to perform a mass spectrometry for an ion originating from the aforementioned sample component or a mass spectrometry for a sample containing the target component.

5. The chromatograph mass spectrometer according to claim 2 or 3, further comprising:

a quantity calculator for determining a quantity of the target component by using the extracted ion chromatogram corresponding to the mass-resolving power selected as the optimal condition by the chromatogram evaluator.

6. The chromatograph mass spectrometer according to claim 1, wherein:

the mass spectrometer has a single quadrupole mass filter, and the controller conducts a mass spectrometry of the target component in a selected ion monitoring measurement mode.

7. The chromatograph mass spectrometer according to claim 1, wherein:

the mass spectrometer has two of the quadrupole mass filters respectively provided before and after a collision cell, and the controller conducts an MS/MS analysis of the target component in a multiple reaction monitoring measurement mode or selected reaction monitoring measurement mode while changing a combination of the mass-resolving power of the first quadrupole mass filter and the mass-resolving power of the second quadrupole mass filter.

8. The chromatograph mass spectrometer according to claim 3, further comprising:

an automatic analysis-condition setter for setting, as an analysis condition, the mass-resolving power selected as the optimal condition by the chromatogram evaluator, so as to perform a mass spectrometry for an ion originating from the aforementioned sample component or a mass spectrometry for a sample containing the target component.

9. The chromatograph mass spectrometer according to claim 3, further comprising:

a quantity calculator for determining a quantity of the target component by using the extracted ion chromatogram corresponding to the mass-resolving power selected as the optimal condition by the chromatogram evaluator.

10. The chromatograph mass spectrometer according to claim 3, wherein:

the mass spectrometer has a single quadrupole mass filter, and the controller conducts a mass spectrometry of the target component in a selected ion monitoring measurement mode.

11. The chromatograph mass spectrometer according to claim 3, wherein:

the mass spectrometer has two of the quadrupole mass filters respectively provided before and after a collision cell, and the controller conducts an MS/MS analysis of the target component in a multiple reaction monitoring measurement mode or selected reaction monitoring measurement mode while changing a combination of the mass-resolving power of the first quadrupole mass filter and the mass-resolving power of the second quadrupole mass filter.

* * * * *